US005423862A

United States Patent [19]

Clarke et al.

[11] Patent Number: 5,423,862

[45] Date of Patent: Jun. 13, 1995

[54] ORTHOPEDIC TREATMENT APPARATUS

[75] Inventors: James M. Clarke; Bruce D. Uhler; James M. Steinke, all of Longwood; Dana Jones, Clermont, all of Fla.

[73] Assignee: Mediflex Systems, Inc., Longwood, Fla.

[21] Appl. No.: 11,135

[22] Filed: Jan. 29, 1993

[51] Int. Cl.[6] .................... A61M 1/02

[52] U.S. Cl. .................... 606/242; 5/608; 602/32; 601/86; 601/100

[58] Field of Search .................... 602/32, 38, 39; 606/242–245; 5/609, 618, 608; 601/98, 86, 100; 128/845

[56] References Cited

U.S. PATENT DOCUMENTS

| | | | |
|---|---|---|---|
| 1,011,038 | 12/1911 | Davenport . | |
| 1,076,475 | 10/1913 | Albright . | |
| 1,400,546 | 12/1921 | Holme . | |
| 1,453,013 | 6/1919 | Koenigkramer . | |
| 1,830,071 | 1/1929 | Patton | 606/242 |
| 1,950,948 | 11/1929 | Murray | 606/242 |
| 2,494,746 | 3/1939 | Colston | 606/245 |
| 2,749,911 | 7/1952 | Griffin | 606/242 |
| 3,041,122 | 9/1960 | Weickgenannt | 5/618 |
| 3,620,210 | 3/1969 | Annas | 606/245 |
| 3,998,218 | 12/1976 | Lane et al. . | |
| 4,579,109 | 4/1986 | Lundblad . | |
| 4,865,303 | 9/1989 | Hall | 5/618 |
| 5,282,835 | 2/1994 | Wright | 606/242 |

*Primary Examiner*—Robert A. Hafer
*Assistant Examiner*—David J. Kenealy
*Attorney, Agent, or Firm*—William M. Hobby, III

[57] ABSTRACT

An orthopedic treatment apparatus has a frame having a first movable platform having a platform frame movably attached to the frame for a reciprocating motion on a first pivot in a generally vertical motion. The first movable platform is also movably attached to said platform frame for a generally horizontal reciprocating motion on a second pivot. A first drive motor is attached to the frame and coupled to the first movable platform for driving the platform in a reciprocating motion relative to the frame while a second drive motor is attached to the first movable platform frame and coupled to the platform for moving the platform in a generally horizontal reciprocating motion relative to the frame. A second platform is movably attached to the frame and movable relative thereto and is driven by a third drive motor attached to the frame and operatively coupled to the second platform to move the platform relative to the frame in a generally oscillatory controlled pattern so that the orthopedic treatment apparatus moves plural portions of a patient through a plurality of compound motions which are adjustable as to cycle time for each motion which motions occur about pivots projected to regions within the spinal column.

14 Claims, 4 Drawing Sheets

ORTHOPEDIC TREATMENT APPARATUS

BACKGROUND OF THE INVENTION

The present invention relates to an orthopedic treatment table and especially to such a table which can simultaneously move a patient's body through multiple compound motions.

In the past, it has been common to provide various types of passive exercise devices which place a patient on a table or other exercise device which in turn moves portions of the patient's body through predetermined motions. These devices use electric motors and mechanisms, such as cams, links, and belts, to move portions of the patient's body. For instance, a passive exercise device for the legs might move each leg separately vertically in an up and down motion without the patient having to lift his own leg. Such devices are used in salons where a series of separate passive exercise devices place different portions of a body through different motions for exercising and toning the body. Similar devices have also been suggested by chiropractors and orthopedic surgeons as well as osteopaths for moving the body in certain predetermined motions. These devices are sometimes used with arthritic or other patients recuperating from accidents, strokes, or the like. Typical prior art U.S. patents can be seen in the patent to Annas, No. 3,620,210, for a sacroiliac rotator which has a table having a platform with motion provided on one end of the table in a generally horizontal back and forth reciprocation to move the lower part of the body relative to the upper part of the body with the movement of the body being at the pelvic or sacroiliac region. This table also provides for a vertical axis movement of the same table portion for moving on the sacroiliac region to bend the body along a common point and with a single motor using a crank mechanism. The Holme Pat. No. 1,400,546, shows an osteopathic treatment table for placing a patient in a variety of positions by the manual shifting of one end of the table in both horizontal and vertical directions and then locking the table in different positions. Similarly, the Davenport Pat. No. 1,011,038, shows a surgical operating table in which each end of the table can be rotated in a horizontal plane manually to position the patient. The Koenigkramer Pat. No. 1,453,013, shows a treatment table in which the table can be manually shifted in vertical and horizontal planes to position the patient. The Patton Pat. No. 1,830,071, is for a universal treatment table for use by osteopaths and chiropractors in different types of treatment and allows each end of the table to be shifted between vertical positions on pivots and allows one end of the table to be moved in a horizontal direction and also provides for shifting of the center table portion. The Murray Pat. No. 1,950,948, shows an osteo rotor providing for placing a patient under tension and also provides a circular motion to one end of the table. The Colston Pat. No. 2,494,746, shows a body manipulating table which allows for motorized vertical motion on one end of the table with the patient's legs strapped to the other end. The Lane et al. Pat. No. 3,998,218, shows a chiropractic table which enables a doctor to raise or lower individual cushions on the table while treating the patient on the table. The Lundblad Pat. No. 4,579,109, shows an apparatus for treating back ailments which allows tension to be placed on the patient while providing a motorized movement to one end of the table. The Albright Pat.

No. 1,076,475, shows an early version of a revolving leaf treating table.

In contrast to these prior art patents, the present invention is for an orthopedic treatment table which allows a compound motion of each end which are individually controllable by cycle time as to vertical and horizontal motion to provide a compound motion on one end of the body while providing a compound oscillatory motion to the other end to provide greater flexibility to the compound motions and infinite variations in the cycles, which compound motions are directed to pivot within selected regions of the spinal column.

SUMMARY OF THE INVENTION

An orthopedic treatment apparatus has a frame having a first movable platform having a platform frame movably attached to the frame for a reciprocating motion on a first pivot having an intersection located in a region of the spinal column in a generally vertical motion. The first movable platform is movably attached to the platform frame for a generally horizontal reciprocating motion on a second pivot having an intersection within a region of the spinal column. A first drive motor is attached to the frame and coupled to the first movable platform for driving the platform in the reciprocating motion relative to the frame while a second drive motor is attached to the first movable platform frame and coupled to the platform for moving the platform in a generally horizontal reciprocating motion relative to the frame. A second platform is movably attached to the frame and movable relative thereto and is driven by a third drive motor attached to the frame and operatively coupled to the second platform to move the platform relative to the frame in a generally oscillatory motion about a pivot projected to be within a second region of the spinal column so that the orthopedic treatment apparatus moves plural portions of a patient through a plurality of compound motions which are adjustable by cycle time for each motion.

BRIEF DESCRIPTION OF THE DRAWINGS

Other objects, features, and advantages of the present invention will be apparent from the written description and the drawings in which.

DESCRIPTION OF THE PREFERRED EMBODIMENT

Figure 1:
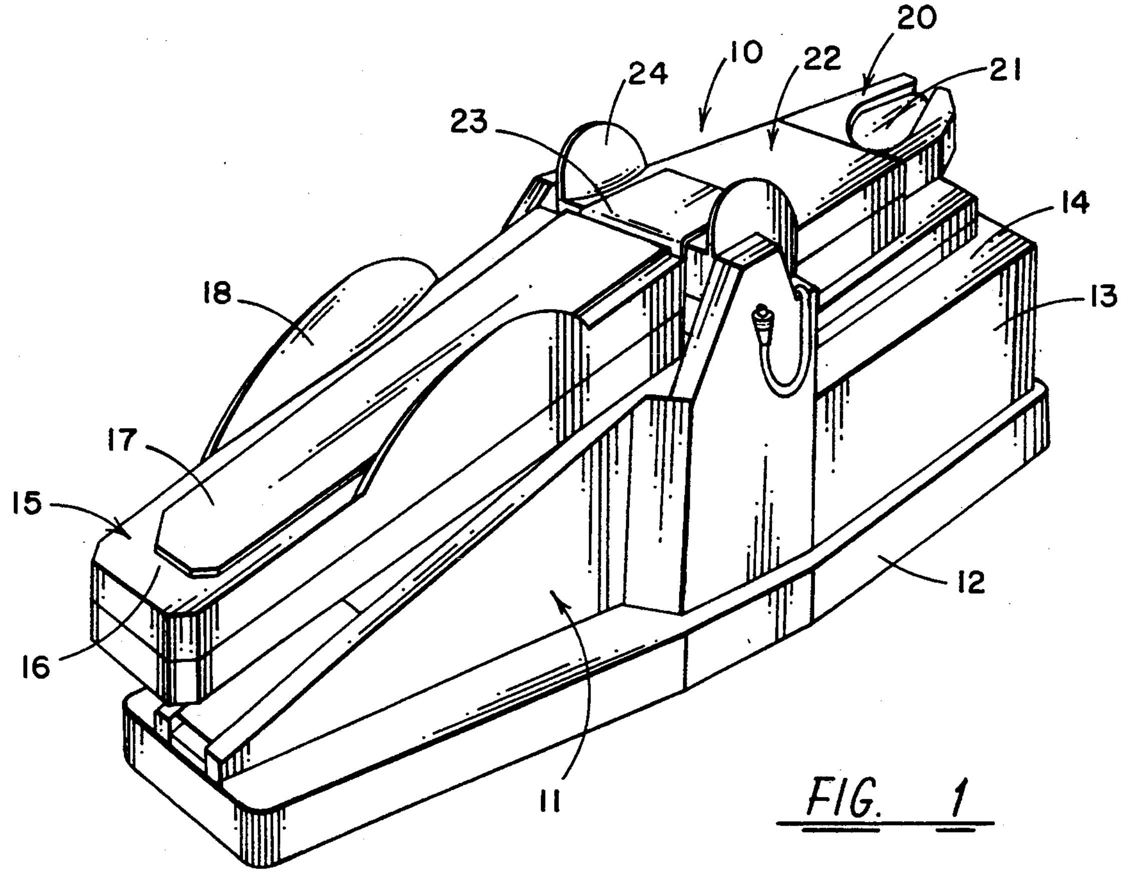
FIG. 1 is a perspective view of an orthopedic treatment apparatus in accordance with the present invention.
Figure 2:
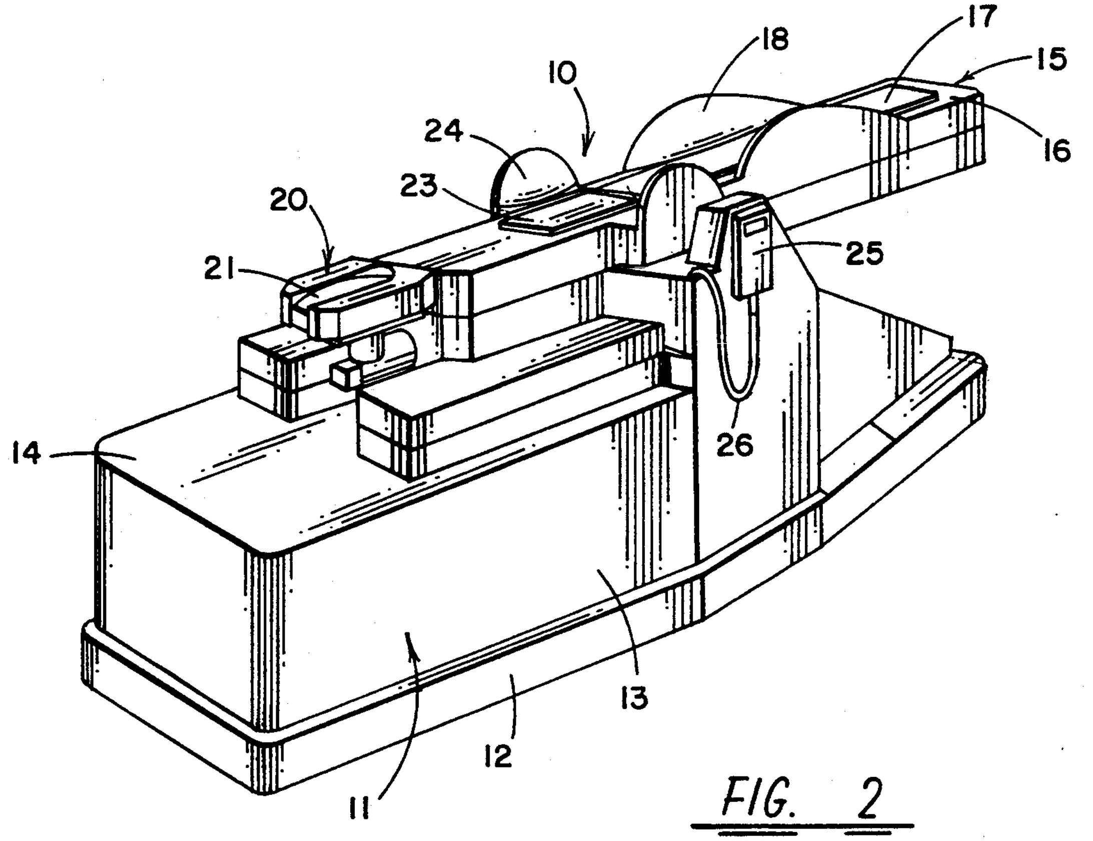
FIG. 2 is a perspective view of the orthopedic treatment apparatus taken from the other side of FIG. 1.

Referring to the drawings and especially to FIGS. 1 and 2, an orthopedic treatment apparatus of table 10 is illustrated in perspective views having a cover 11 having a base cover portion 12, side cover portion 13, and top cover portion 14. The orthopedic table has a movable platform portion 15 which is for supporting a leg which has a cover 16 and a supporting pad 17 along with side supports 18 for holding the legs of a patient laying thereon in position during movement of the platform of table portion 15. A second platform or head supporting portion 20 has a support for supporting the head during motion of the platform 20. A fixed portion of the platform or patient supporting table 22 is also covered as is the fixed portion 23 having the side supports 24.

In operation, a patient is placed on the table 10 with his legs extending on the pads 17 between the side supports 18 and his head resting on the head support platform 20 in the head support 21. The operator can use the control 25 to program the movements of the platform portion 15 and the movement of the platform portion 20 through separate compound movement cycles at predetermined cycle movements in both vertical and horizontal directions which pivot in the plane of the spinal column and, at the same time, set the timer for a predetermined time of operation. Cable 26 is connected from the control 25 to control electric motors through relays. Three separate motors are utilized for different movement operations so that the cycles can be separately controlled in three different movement directions for the two platforms 15 and 20. Thus, a patient can have his leg portion moved relative to the hips which may be positioned on the portion 23 of the platform while the platform 15 moves up and down in a vertical direction and can simultaneously or alternately move left and right in a horizontal direction. Each control for separate cycles of rotation or speeds and each control for the link of vertical up and down movement or horizontal left and right movement is entered by keypad into a local computer self-contained within the apparatus. The upward vertical movement is for lumbar flection about a pivot located within the spinal column and the platform may be raised 35° from a horizontal while the down motion of the platform 15 provides a lumbar extension and may be 10° from horizontal for a total of 45° vertical movement of the platform 15. Each movement can be controlled for speeds from 1 to 15 cycles per minute and can be set to operate on a timed duration of anywhere between 1 and 60 minutes. Simultaneously with or alternate to the vertical motion of the platform 15, the head supporting portion can be rotated vertically about a pivot projected to the spinal column for cervical flection of up to 15° vertically or for cervical extension by downward movement of 15° from horizontal. Each movement of the platform can have the speed varied from 1 to 15 cycles per minute and can be set for a time duration of between 1 and 60 minutes and separately controlled from the operation of the platforms. In addition, the horizontal right to left movement of the platform 15 can be used for lumbar lateral flection and is controlled by a separate motor with a range from 15° to the left and right from a center null position and using a speed of between 1 and 15 cycles per minute for a timed duration of from 1 to 60 minutes. The motion and speed of each of the platforms is controlled as directed by the orthopedic doctor as needed.

Figure 3:
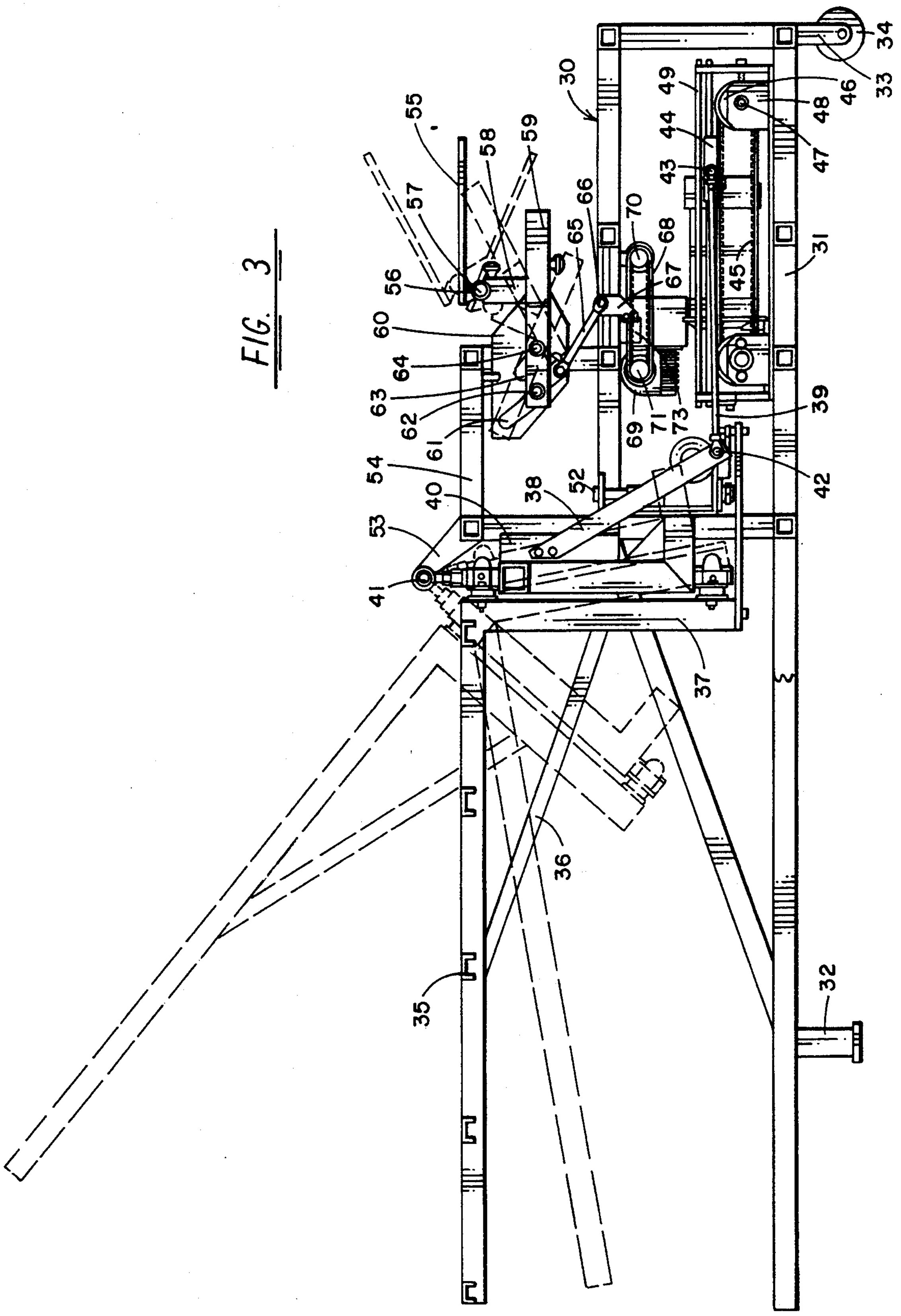
FIG. 3 is a side elevation of the orthopedic treatment apparatus of FIGS. 1 and 2 having the cover removed and having phantom views illustrating movement.
Figure 4:
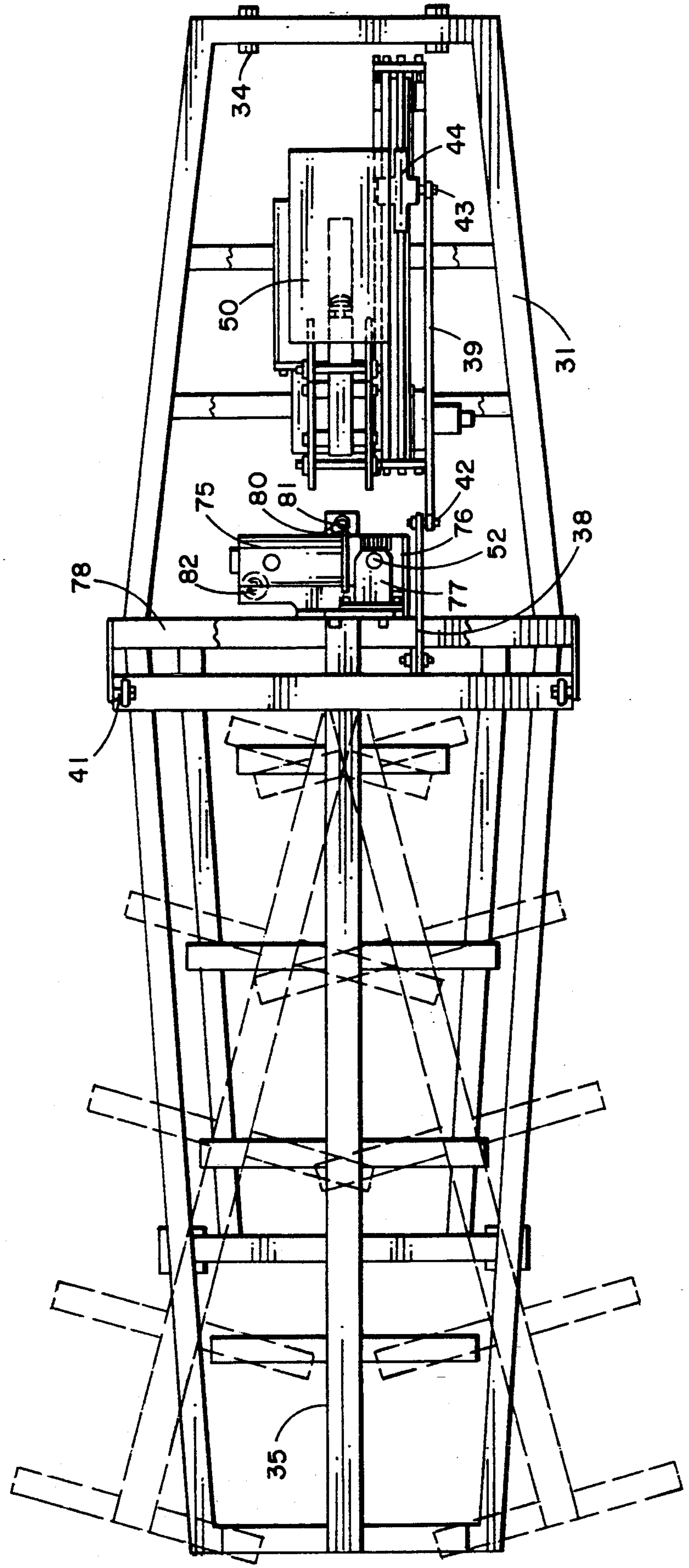
FIG. 4 is a top plan view of an orthopedic treatment apparatus having the cover and portions removed and showing the horizontal movement in phantom.
Figure 5:
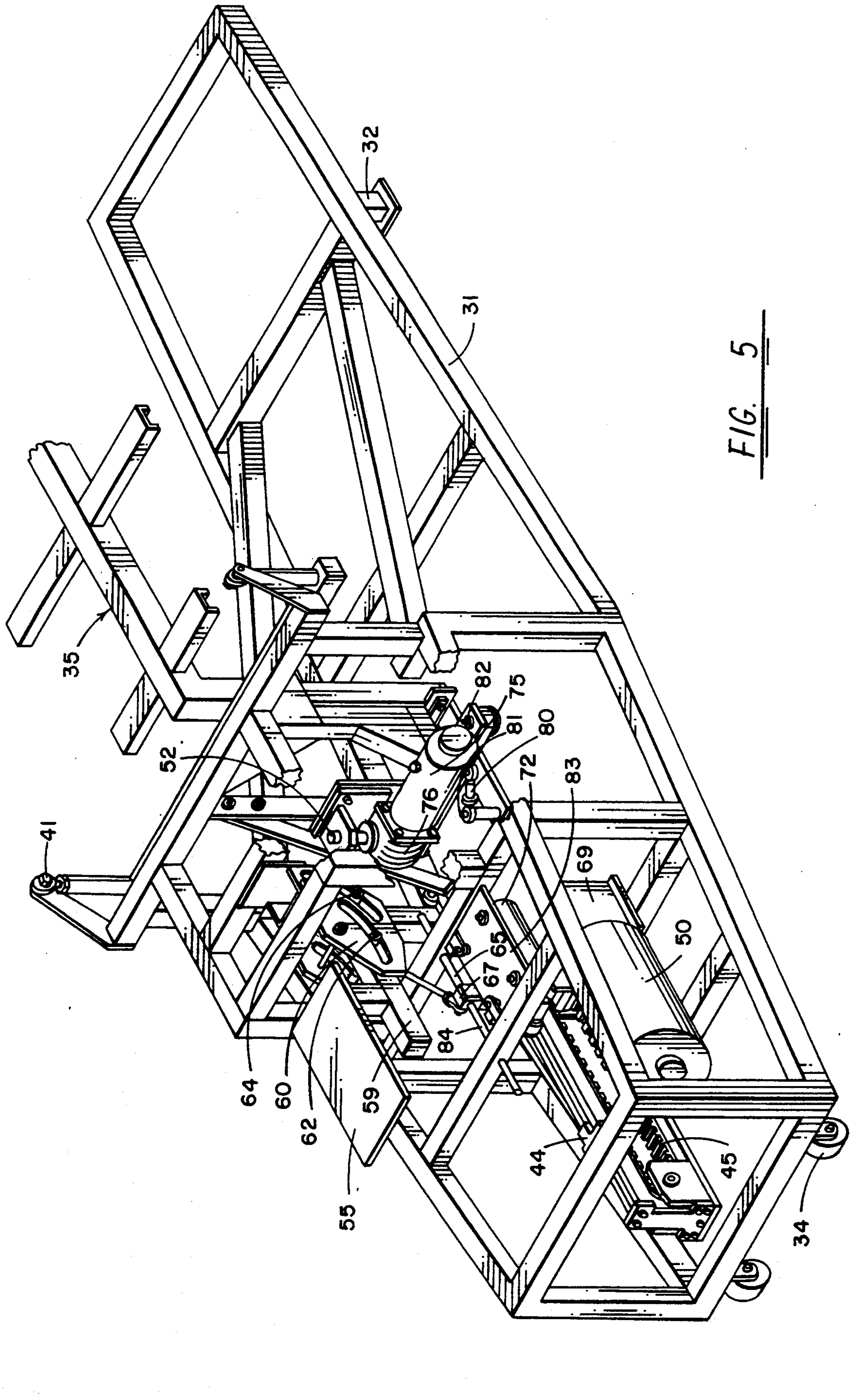
FIG. 5 is a partial perspective view of the orthopedic treatment apparatus with the cover removed.

Turning now to FIGS. 3, 4 and 5, the operation of each of the compound movements is illustrated in which the apparatus has a rigid frame 30 having a base frame 31 and a plurality of legs 32, two of the legs 33 having wheels 34 for ease of movement of the orthopedic treatment table. The platform 15 of FIGS. 1 and 2 is supported by a steel frame 35 having a rigid steel brace 36, both supported on a vertical steel platform frame member 37. The up and down motion is controlled by moving the vertical frame portion 37 and the rest of the frame with a rigid member 38 attached to a frame portion 40 which rotates on a pair of pivots 41 which lie in the plane of the spinal column to allow the frame 35 to move up and down in a vertical (rotation) direction. The link member 38 is rigidly attached to the frame portion 40 on one end but is moved by a link 41 movably attached with a pin 42 to the member 38 at the other end thereof. The rigid link 39 is attached at the other end thereof with a pin 43 to a shuttle member 44 which in turn is attached to a cog belt 45 which belt rides on a cylindrical idler gear 46 supported in a journal 47 to a frame member 48 which is attached to the frame 30. The cog belt is held at the other with a gear attached to the shaft of a gear box 69 driven by the reversible motor 50. The gear box shaft is supported in journal 51 and a frame portion 49 forms a track for the shuttle member 44 as the cog belt 45 is driven back and forth by the electric motor 50. The frame 35 for the platform is also supported for horizontal movement by the shaft 52 as described hereinafter. While the shafts 41 are supported in bearings to the frame member 53, the rigid frame portion 54 allows the patient to be supported on a platform 26 attached to the frame 54.

The motion of the head platform 20 (FIG. 1) can be seen having the "second" platform portion 55 supported by short rigid links 56 to a pivot 57 held on a frame member 58 to the horizontal frame portion 59 which has a camming member 60 having a camming slot 61 for a cam follower 62 and a cam slot 63 with a cam follower 64 riding therein. The cam followers are both attached to the horizontal frame portion 59. The horizontal frame portion 59 is attached to a link 6B which is attached with a pin 66 to a moving shuttle member 67 driven by a cog belt 68 riding on a rotating cog gear 70 at one end and a cog gear 71 on the other end attached to a separate gear box 69 and reversible electric motor 72 which in turn is rigidly attached to the frame 30 which drives the cog belt 68 and in turn drives the member 73 and 67 to drive the link 6B to drive the member B9 to direct the platform 55 through a predetermined motion responsive to the operation of the motor 72 to move the shuttle member 67 back and forth, as can be more clearly seen in FIG. 5. Movement of the platform frame member 59 follows a predetermined path governed by the cam slots 60 and 63 in member 60 to force the cam followers 62 and 64 attached to member 59 in the set pattern effectively.

In FIGS. 4 and 5, the motor 75 has a gear box 76 for driving shaft portion 52 to move the platform frame 35 and the platform 15 (of FIG. 1) in a horizontal, left and right direction responsive to the cycle program for the motor 75. The frame portion 77 as well as the motor 75 are attached to the first movable platform frame 78 of the frame 35 to move with the frame so that the motor 75 and gear box 76, move with the frame 35 in a vertical direction while driving the frame in a horizontal movement, left and right, as shown in FIG. 4 in the phantom views. The speed of the motor 75 and the speed of the motor 50 are separately controlled so that the speed of the vertical movement, up and down, and the left and right are separately controlled for a compound movement based on different cycles to provide different benefits for different patients as prescribed by the physician. FIG. 4 also more clearly shows the linkage member 38 movably connected with the pin 42 to the linkage arm 41 and the arm 41 connected with the pin 43 to the shuttle 44 which rides on the cog belt 45. The motor 75 can be seen in this view as having the link member 80 movably pinned with the pin 81 at one end and 82 at the other end to support the horizontal or back and forth movement of the frame 35.

FIG. 5, on the other hand, shows a motor 75 connected to the gear box 76 and connected to the shaft 52 for controlling the horizontal movement of the frame 35. Similarly, the motor 50 controlling the gear box 49 is illustrated for driving the cog belt 45 to drive the shuttle 44 for moving the frame 35 in an up and down direction on the pair of pivots 41. This view also shows the operation of the motor 72 connected to the frame plate 83 for driving the shuttle member 67 riding on a shaft 84 to move the link members 65 to in turn drive the frame 59 to follow the pair of cam slots in the cam plates 60 with the cam followers 62 and 64 riding therein for controlling the head platform member 55 and head platform 20 (FIGS. 1 and 2).

It should be clear at this time that the operation of an orthopedic treatment table has been provided which provides orthopedic treatment to patients in accordance with an orthopedic physician's prescription which can be programmed for a series of compound movements of the patient, simultaneously or alternately moving the head in a predetermined fashion at one speed or cycle of movement and controlling the movement of the legs and lower torso in a vertical reciprocating motion and/or alternately in a horizontal reciprocating motion under different speeds to provide a different variety of compound motions each providing pivot locations within specific regions of the spinal column. This operation is provided by three separate motors driving three separate drive mechanisms to provide treatment tailored to a specific patient's orthopedic diagnosis. However, it should also be clear that the present invention is not to be considered limited to the forms shown which are to be considered illustrative rather than restrictive.

I claim:

1. An orthopedic treatment apparatus comprising:

a main frame;

a first movable platform frame movably attached to said main frame on a first pivot;

a first drive motor attached to said main frame, said first drive motor driving a belt having a shuttle connected to a linkage which linkage is coupled to said first movable platform frame for driving said first movable platform frame in a generally vertically reciprocating motion relative to said main frame;

a second movable platform frame movably attached to said first movable platform frame on a second pivot;

a second drive motor attached to said first movable platform frame and coupled to said second movable platform frame for moving said second movable platform frame in a generally horizontal reciprocating motion;

a first platform attached to said second movable platform frame and movable in a generally horizontal reciprocating motion with said second movable platform frame and in a generally vertical motion with said first movable platform frame to thereby form a compound motion of said first platform;

a second platform being movably attached to said main frame and movable relative thereto; and a third drive motor attached to said main frame and operatively coupled to said second platform to move said platform relative to said main frame; whereby said first and second platforms have a controlled motion to move a patient simultaneously through a plurality of compound motions.

2. An orthopedic treatment apparatus in accordance with claim 1 in which said second drive motor is mounted to said first platform frame and is coupled to said second platform frame to move said second platform frame in a horizontal reciprocating motion.

3. An orthopedic treatment apparatus in accordance with claim 2 in which said third drive motor is attached to said main frame and is coupled through a linkage to said second platform to move said second platform in a predetermined motion.

4. An orthopedic treatment apparatus in accordance with claim 3 in which said second platform linkage includes a cam guided second platform frame member to guide said second platform through a predetermined motion.

5. An orthopedic treatment apparatus in accordance with claim 4 in which said second platform cam guided second platform frame member includes a pair of cam plates each having a pair of arcuate camming slots therein and said second platform member has a pair of cam followers mounted thereto riding in said cam plate camming slots.

6. An orthopedic treatment apparatus in accordance with claim 5 in which said first platform first motor can be controlled to vary the vertical motion through a cycle between 1 and 15 cycles per minute.

7. An orthopedic treatment apparatus in accordance with claim 6 in which said second drive motor has a controller to vary the horizontal motion through a cycle between 1 and 15 cycles per minute.

8. An orthopedic treatment apparatus in accordance with claim 7 in which said third drive motor has a controller to vary the oscillatory motion through a cycle between 1 and 15 cycles per minute,

9. An orthopedic treatment apparatus in accordance with claim 8 in which said first and second drive motors have a timer to vary the operating time from 1 to 60 minutes,

10. An orthopedic treatment apparatus in accordance with claim 9 in which said third drive motor has a timer to vary the operating time from 1 to 60 minutes,

11. An orthopedic treatment apparatus in accordance with claim 10 in which said first movable platform frame has vertical movement from $-10$ to $+40$ degrees in a generally vertical motion.

12. An orthopedic treatment apparatus in accordance with claim 11 in which said second platform frame has horizontal movement from 15 degrees to each side of a horizontal null position.

13. An orthopedic treatment apparatus in accordance with claim 1 including control means for separately controlling said first, second and third drive motors for selectively controlling the movement of said first and second platforms.

14. An orthopedic treatment apparatus in accordance with claim 1 in which said first and second platform frames first and second pivots are positioned in a predetermined position relative to the spine of a patient thereon to provide a predetermined spinal movement.

* * * * *